US011745361B2

(12) United States Patent
Kimura et al.

(10) Patent No.: US 11,745,361 B2
(45) Date of Patent: Sep. 5, 2023

(54) MANIPULATOR AND JOINT STRUCTURE THEREOF

(71) Applicant: OLYMPUS CORPORATION, Hachioji (JP)

(72) Inventors: Kayuri Kimura, Saitama (JP); Shuya Jogasaki, Tokyo (JP); Hiroyuki Takayama, Tokyo (JP); Noriaki Yamanaka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 759 days.

(21) Appl. No.: 16/709,313

(22) Filed: Dec. 10, 2019

(65) Prior Publication Data

US 2020/0114527 A1    Apr. 16, 2020

Related U.S. Application Data

(63) Continuation of application No. PCT/JP2017/022894, filed on Jun. 21, 2017.

(51) Int. Cl.
*A61B 17/062* (2006.01)
*B25J 15/08* (2006.01)
(Continued)

(52) U.S. Cl.
CPC ............ *B25J 15/08* (2013.01); *A61B 17/062* (2013.01); *A61B 34/71* (2016.02); *B25J 17/025* (2013.01); *B25J 17/0241* (2013.01)

(58) Field of Classification Search
CPC ............ A61B 34/71; A61B 2017/2939; B25J 17/025; B25J 15/08; B25J 9/06; B25J 9/065
See application file for complete search history.

(56) References Cited

U.S. PATENT DOCUMENTS 5,062,673 A * 11/1991 Mimura ............... B25J 15/0009
623/64
5,710,878 A * 1/1998 McCoy ................... G06T 17/00
345/589
(Continued)

FOREIGN PATENT DOCUMENTS

CN         105899117 A      8/2016
EP           1977713 A2     10/2008
(Continued)

OTHER PUBLICATIONS

May 10, 2022 Office Action issued in Chinese Patent Application No. 201780092215.2.
(Continued)

*Primary Examiner* — Gregory Robert Weber
(74) *Attorney, Agent, or Firm* — Oliff PLC

(57) ABSTRACT

A joint structure of a manipulator includes: swiveling members that are coupled so as to be able to swivel via a rolling contact; shafts that constitute bending joints between the swiveling members and that are parallel to each other; pulleys that are rotatably supported about the shafts; and a connector attached to the shafts so as to be able to swivel about longitudinal axes of the shafts. The connector includes supports that are disposed on axial ends of the shafts so as to sandwich the pulleys therebetween in a direction of the longitudinal axis, and a beam that extends in between the supports to couple the supports to each other.

10 Claims, 17 Drawing Sheets

(51) Int. Cl.
 *A61B 34/00* (2016.01)
 *B25J 17/02* (2006.01)

(56) References Cited

U.S. PATENT DOCUMENTS

| | | | | |
|---|---|---|---|---|
| 5,810,716 | A * | 9/1998 | Mukherjee | B25J 9/102 |
| | | | | 600/141 |
| 7,101,363 | B2 * | 9/2006 | Nishizawa | A61B 34/71 |
| | | | | 606/1 |
| 10,092,359 | B2 * | 10/2018 | Beira | A61B 34/30 |
| 10,245,058 | B2 * | 4/2019 | Omori | A61B 17/29 |
| 10,413,164 | B2 * | 9/2019 | Hyodo | B25J 13/04 |
| 2004/0036438 | A1 * | 2/2004 | Yamagishi | B25J 9/102 |
| | | | | 180/8.6 |
| 2004/0199147 | A1 | 10/2004 | Nishizawa et al. | |
| 2008/0245175 | A1 | 10/2008 | Jinno et al. | |
| 2013/0213170 | A1 * | 8/2013 | Kim | B25J 9/104 |
| | | | | 74/490.01 |
| 2015/0343649 | A1 * | 12/2015 | Galinson | B25J 9/104 |
| | | | | 901/27 |
| 2016/0166347 | A1 | 6/2016 | Kishi | |
| 2016/0316996 | A1 | 11/2016 | Nakayama et al. | |
| 2019/0313882 | A1 * | 10/2019 | Nakayama | A61B 1/008 |

FOREIGN PATENT DOCUMENTS

| | | |
|---|---|---|
| EP | 3040045 A1 | 7/2016 |
| EP | 3095375 A1 | 11/2016 |
| JP | 3912251 B2 | 5/2007 |
| JP | 2008253463 A | 10/2008 |
| JP | 2015042234 A | 3/2015 |
| WO | 2015/029804 A1 | 3/2015 |
| WO | 2018/173278 A1 | 9/2018 |

OTHER PUBLICATIONS

Aug. 15, 2017 International Search Report issued in International Patent Application No. PCT/JP2017/022894.

\* cited by examiner

MANIPULATOR AND JOINT STRUCTURE THEREOF

This is a continuation of International Application PCT/JP2017/022894, with an international filing date of Jun. 21, 2017, which is hereby incorporated by reference herein in its entirety.

The present disclosure relates to a manipulator and a joint structure thereof.

BACKGROUND

A joint structure for a manipulator may include a first member and a second member adapted to swivel with respect to the first member are brought into a rolling contact with gears secured to both the members. The two axial lines of both the gears may be coupled through linking, with pulleys disposed at the two axial lines, and a wire for driving a mechanism on a tip end side may be stretched between the pulleys in a meandering manner is known. There is a need for an improved joint structure.

SUMMARY

An aspect of the present disclosure is directed to a joint structure of a manipulator, including: swiveling members that are coupled so as to be able to swivel via a rolling contact; shafts that constitute bending joints between the swiveling members and that are parallel to each other; pulleys that are rotatably supported about the shafts; and a connector attached to the shafts so as to be able to swivel about longitudinal axes of the shafts. The connector includes supports that are disposed on axial ends of the shafts so as to sandwich the pulleys therebetween in a direction of the longitudinal axis, and a beam that extends in between the supports to couple the supports to each other.

Another aspect of the present disclosure is directed to a manipulator, including: a grip that is provided at a tip end of an elongate insertion part; and a first joint and a second joint that are aligned in series between the insertion part and the grip and that have the aforementioned joint structure. The first joint is disposed on a furthest side at the tip end is able to swivel at an angle that is greater than an angle at which the second joint on a base end side swivels, in a direction opposite to a direction in which the second joint swivels.

DETAILED DESCRIPTION

A manipulator 100 and a joint structure 1 thereof according to an exemplary embodiment will be described below with reference to drawings.

Figure 1:
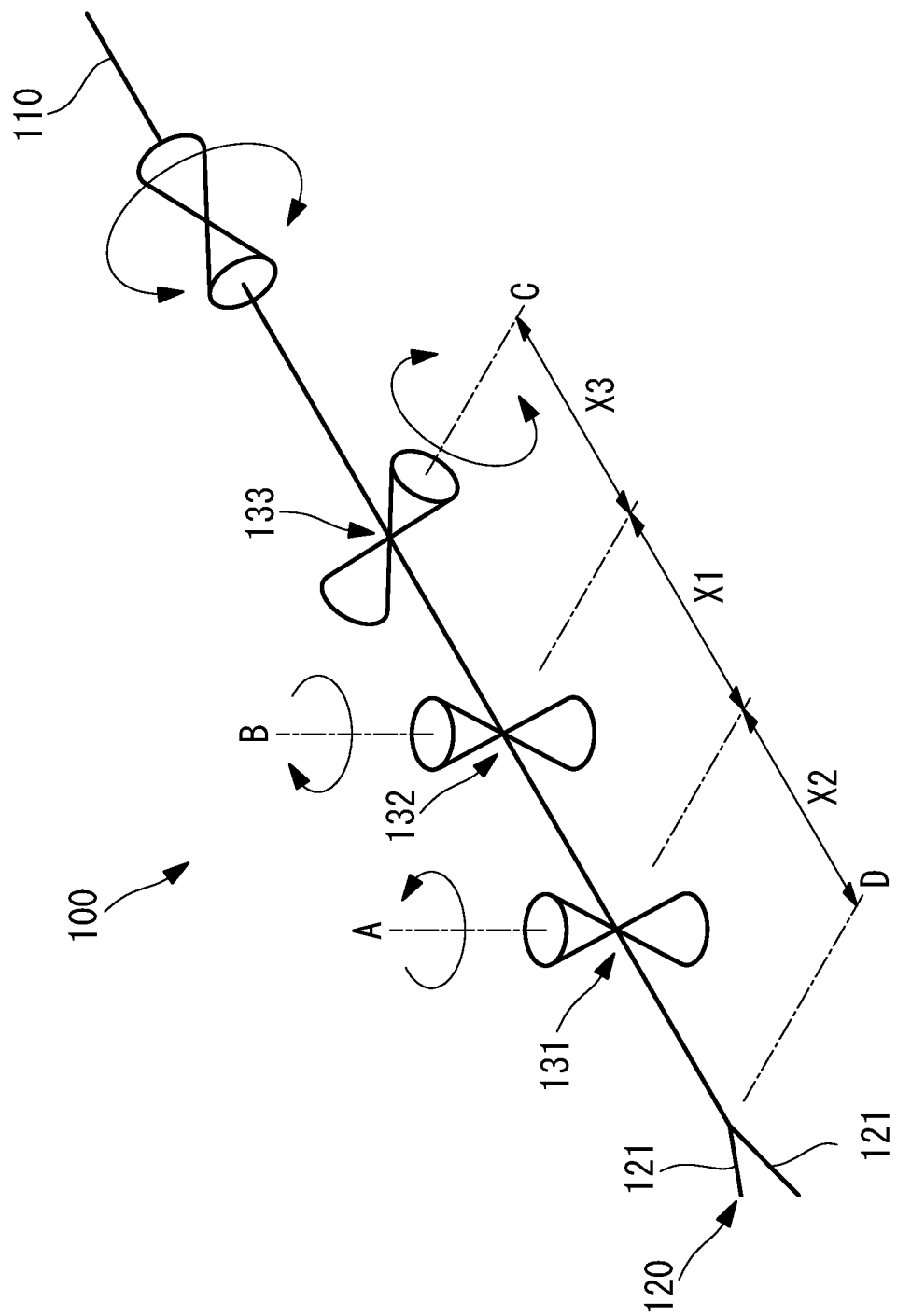
FIG. 1 is a schematic perspective view illustrating an example of a shaft configuration of a manipulator according to an exemplary embodiment.

The manipulator 100 according to the present embodiment includes a gripping part 120 at a tip end of an elongate inserting part 110 and also includes a plurality of joints 131, 132, and 133 in series between the inserting part 110 and the gripping part 120, as illustrated in FIG. 1.

Each of the joints 131, 132, and 133 is a bent joint that causes a first member (swiveling member) 2 disposed on a tip end side to swivel about axial lines A, B, and C that perpendicularly intersect a longitudinal axis of the manipulator 100 with respect to a second member (swiveling member) 3 disposed on a base end side. In an order from the tip end side, the first joint 131 that causes the first member 2 to swivel about a predetermined axial line A with respect to the second member 3, the second joint 132 that allows for the swiveling about an axial line B that is parallel to the axial line A of the first joint 131, and a third joint 133 that allows for the swiveling about an axial line C that is disposed in a skew positional relationship with the axial line B of the second joint 132 are included.

The gripping part 120 is adapted such that facing gripping surfaces are opened and closed to grip an object, for example, a curved needle between the gripping surfaces by causing a pair of gripping pieces 121 to relatively swivel about an axial line D that perpendicularly intersects the longitudinal direction.

The first joint 131 and the second joint 132 can mutually bend the first member 2 in an opposite direction with respect to the second member 3 and satisfy Conditional Expression (1) below:

$$X2 \geq X1 > X3 \quad (1)$$

Here, X1 is a distance between the first joint 131 and the second joint 132, X2 is a distance between the first joint 131 and a base end of the gripping part 120, and X3 is a distance between the third joint 133 and the first joint 131 or the second joint 132 that is closer to the third joint 133.

Figure 2:
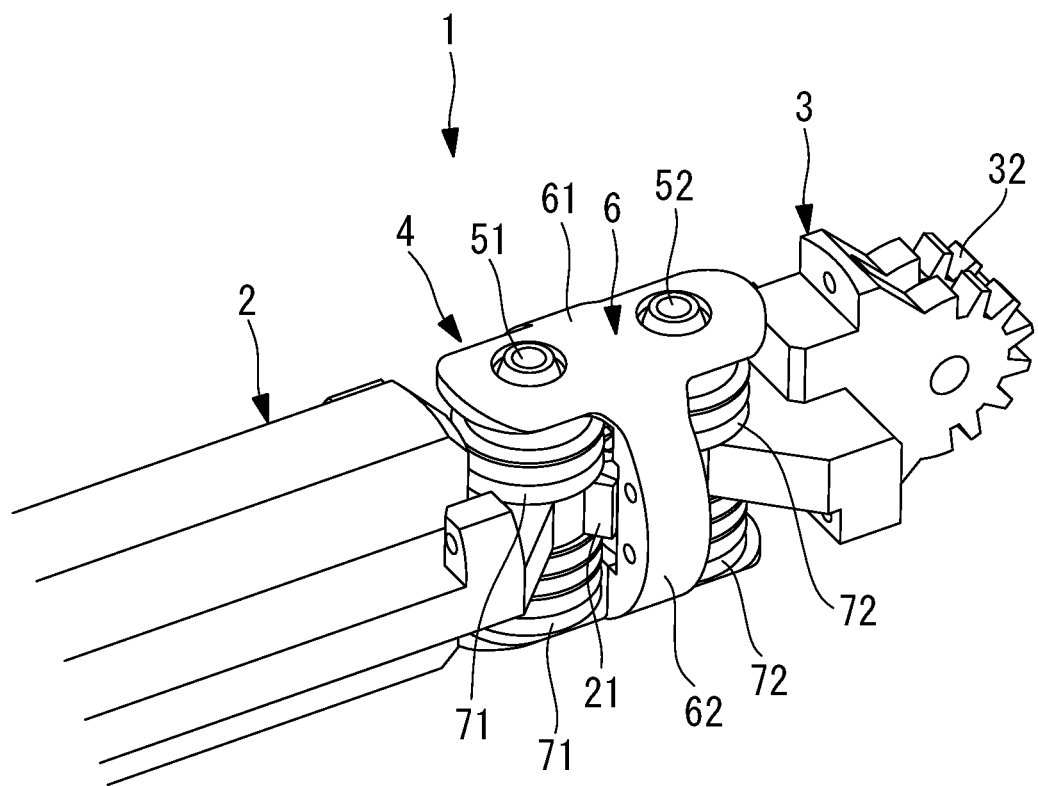
FIG. 2 is a partial perspective view illustrating a joint structure of the manipulator according to an exemplary embodiment.
Figure 3:
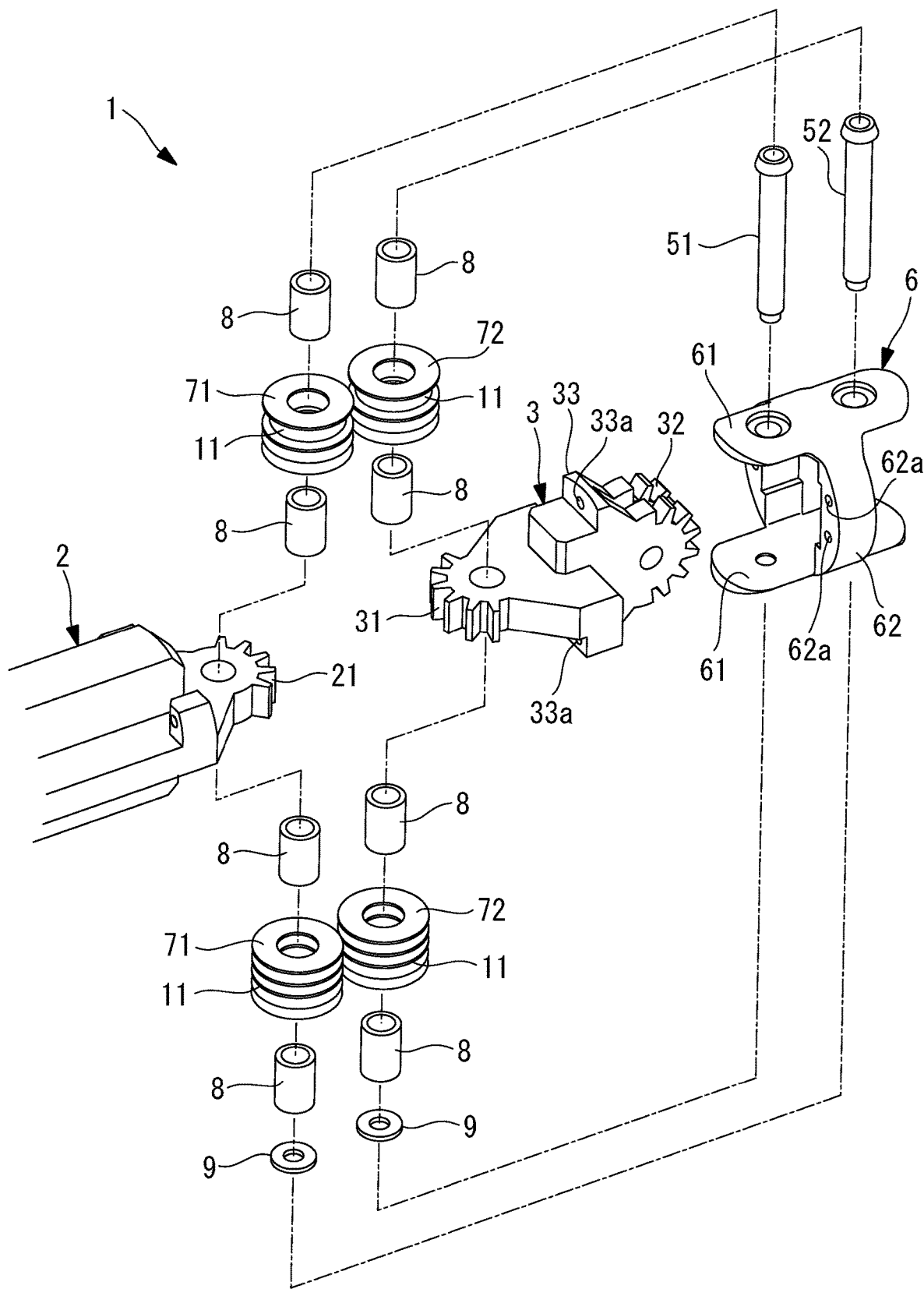
FIG. 3 is an exploded perspective view illustrating the joint structure in FIG. 2.
Figure 4:
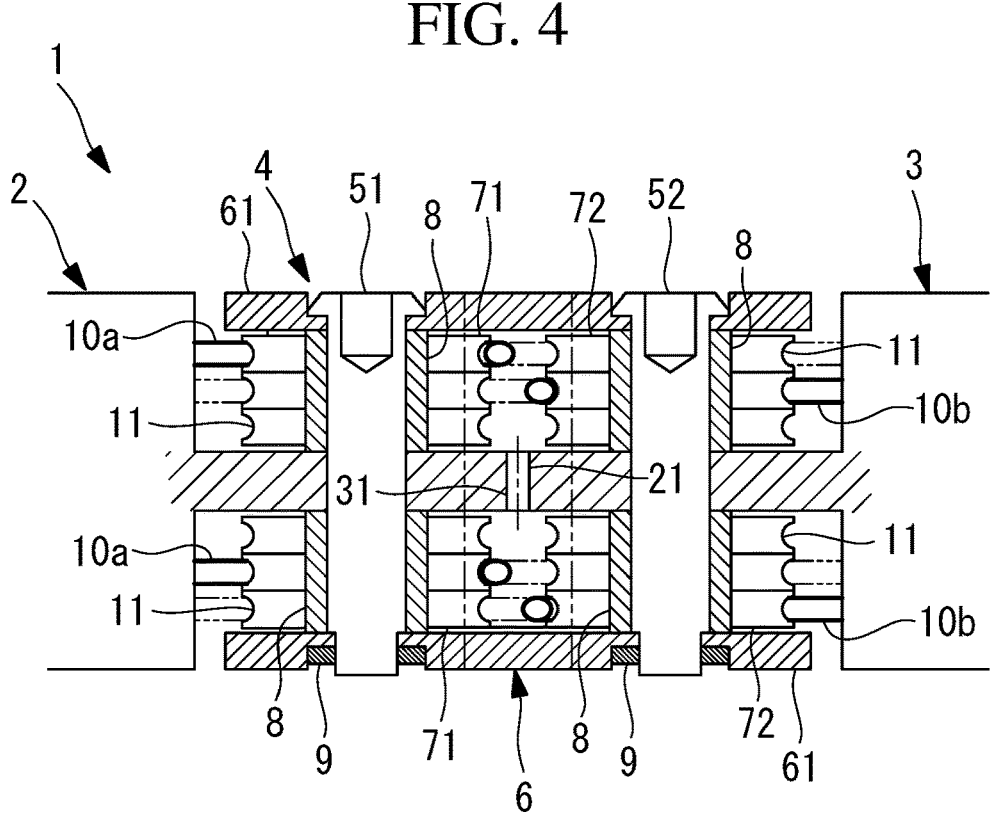
FIG. 4 is a partial vertical sectional view illustrating the joint structure in FIG. 2.

The joint structure 1 of each of the joints 131, 132, and 133 includes a first member 2, a second member 3, two parallel shafts 51 and 52 that form two bending joint parts 4 provided therebetween, a single linking member 6, and pulleys 71 and 72 that are rotatably attached to the respective shafts 51 and 52, as illustrated in FIGS. 2 to 5. In FIGS. 3 and 4, the reference numeral 8 represents a collar that rotatably attaches the pulleys 71 and 72 to the respective shafts 51 and 52. In FIG. 3, the reference numeral 9 represents a stopper that secures the respective shafts 51 and 52 to the linking member 6.

Figure 5:
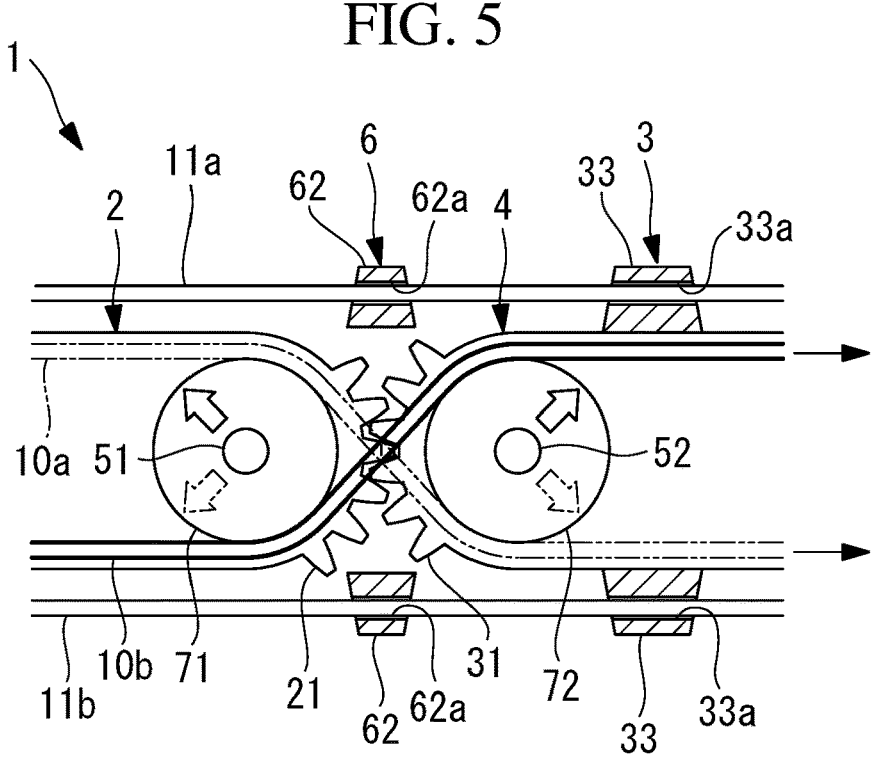
FIG. 5 is a partial side view illustrating a positional relationship of gear parts, pulleys, and a wire in the joint structure in FIG. 2.

The first member 2 includes a first gear part (rolling part) 21 that is formed at a part in a circumferential direction around the shaft 51 disposed at an end as illustrated in FIGS. 3 and 5. The second member 3 includes a second gear part (rolling part) 31 that is formed at a part in the circumferential direction around the shaft 52 disposed at an end and that meshes with the first gear part 21. Also, the second member 3 includes a gear part 32 that is formed on a side opposite to the second gear part 31 so as to be able to swivel in a direction perpendicular to the rotational axis of the second gear part 31 and a coupling part 33 that couples the second gear part 31 to the gear part 32.

The linking member 6 is attached so as to be able to rotate about the shafts 51 and 52 as illustrated in FIGS. 2 and 3. Also, the linking member 6 includes two supporting parts 61 with flat plate shapes that are rotatably attached to both ends of the two shafts 51 and 52 and a coupling part 62 that couples both ends of the supporting parts 61 in a width direction in the vicinity of the center in the longitudinal direction.

Consequently, the linking member 6 has a horizontal sectional shape closed in a ring shape in the vicinity of the center in the longitudinal direction as illustrated in FIG. 3 to achieve support with high rigidity in order for the two supporting parts 61 to be prevented from relatively moving.

Each of the pulleys 71 and 72 is provided with a circumferential groove 11 on which wires 10a and 10b for driving a mechanism disposed on the tip end side using the respective joints 131, 132, and 133 are wound, as illustrated in FIGS. 4 and 5. The number of circumferential grooves 11 differs depending on the number of mechanisms disposed on the tip end side. In the example illustrated in FIG. 5, one wire 10a is wound around the circumferential groove 11 of any of the two pulleys 71 and 72 so as to alternately meander, and the other wire 10b is wound around the circumferential groove 11 of the other one of the two pulleys 71 and 72 so as to alternately meander in a direction opposite to that of the one wire 10a.

Also, the coupling parts 33 and 62 of the second member 3 and the linking member 6 include through-holes 33a and 62a through which two manipulation wires 11a and 11b with tip ends secured to the first member 2 are caused to penetrate, as illustrated in FIGS. 3 and 5. The manipulation wires 11a an 11b are provided in each of the joints 131, 132, and 133. By pulling any of the two manipulation wires 11a and 11b on the base end side, it is possible to cause a moment in a forward and reverse directions around the longitudinal axis of the shaft 51 to act on the first member 2, to which the tip ends of the wires 10a and 10b are connected, using a traction force.

Effects of the manipulator 100 and the joint structure 1 thereof according to the present embodiment configured as described above will be described below.

According to the joint structure 1 in the present embodiment, it is possible to cause the first member 2 to swivel in two directions by pulling the first member 2 from the side of the second member 3 using any of the two manipulation wires 11a and 11b when the first member 2 is to be caused to swivel with respect to the second member 3.

Figure 6:
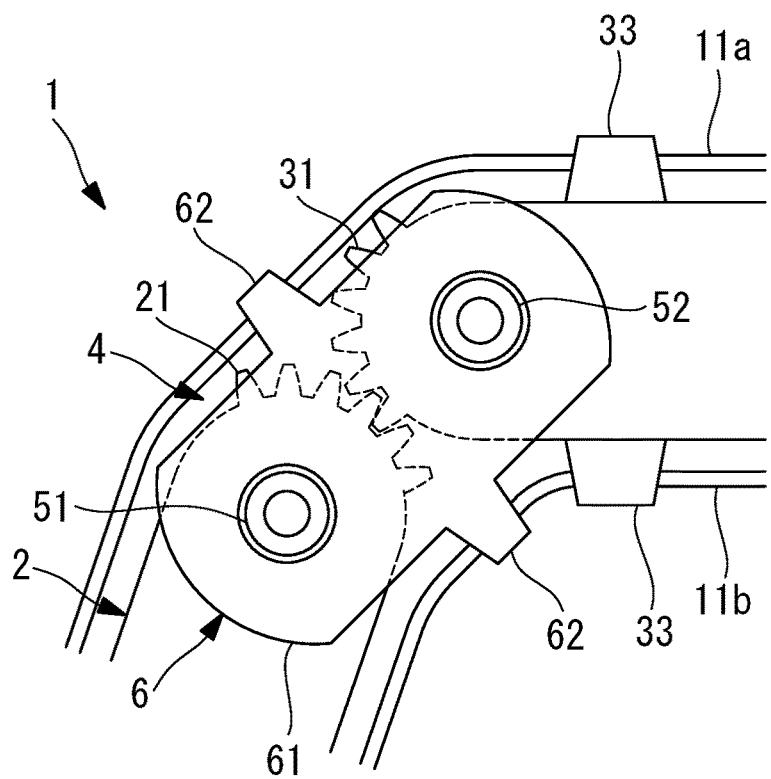
FIG. 6 is a side view illustrating a state in which a first member is caused to swivel with respect to a second member in the joint structure in FIG. 5.

In this case, since the first gear part 21 of the first member 2 that meshes with the second gear part 31 provided at the second member 3 rolls about the longitudinal axis of the shaft 51, the position of the shaft 52 is translated around the longitudinal axis of the shaft 51, the linking member 6 rotates about the longitudinal axis of the shaft 51, and also, the first member 2 rotates about the longitudinal axis of the shaft 52 at the tip end of the linking member 6, as illustrated in FIG. 6.

Consequently, a swiveling angle of the first member 2 with respect to the second member 3 is divided into two angles, namely a swiveling angle of the second member 3 with respect to the linking member 6 and a swiveling angle of the linking member 6 with respect to the first member 2.

That is, the second member 3 is caused to swivel with respect to the first member 2 at an angle obtained by summing up the swiveling angle of the linking member 6 with respect to the first member 2 and the swiveling angle of the second member 3 with respect to the linking member 6.

As a result, there is an advantage that it is possible to reduce relative swiveling angles between the first member 2 and the linking member 6 and between the linking member 6 and the second member 3, which are adjacent to each other, to avoid an interference, and thereby to cause the second member 3 to swivel with respect to the first member 2 at a large swiveling angle.

In this case, according to the joint structure 1 in the present embodiment, the linking member 6 is configured in a ring shape with a closed transverse section at the central position in the longitudinal direction by the two supporting parts 61 that support both ends of the two shafts 51 and 52 and the coupling part 62 that couples these supporting parts 61. Consequently, rigidity significantly increases as compared with that of joint structure in which no coupling part 62 is provided. Also, the pulleys 71 and 72 are disposed at the shafts 51 and 52 that are disposed between the two supporting parts 61 of the linking member 6 with rigidity enhanced in this manner.

As a result, since the shafts 51 and 52 are supported at both ends thereof by the supporting parts 61 by the traction force being applied to the wires 10a and 10b wound around the pulleys 71 and 72 and the wires 10a and 10b pressing the pulleys 71 and 72 in the radial direction as represented by the arrow in FIG. 5 even if a bending force acts on the shafts 51 and 52 that support the pulleys 71 and 72, there is an advantage that the shafts 51 and 52 are brought into a double-supported beam form, rigidity with respect to bending significantly increases as compared with a joint structure in which a cantilever form is employed, and the shafts 51 and 52 can thus be prevented from falling.

That is, since the shafts 51 and 52 are prevented from falling by the linking member 6 with high rigidity although the bending force acts on the shafts 51 and 52 in different directions by the plurality of wires 10a and 10b as illustrated in FIG. 5, it is possible to maintain the shafts 51 and 52 and the linking member 6 in a sound state even if a large traction force is applied to the wires 10a and 10b. Therefore, it is possible to generate a large gripping force with the gripping part 120 and thereby to more reliably grip an object such as a curbed needle.

Also, according to the joint structure 1 in the present embodiment, since the first member 2 and the second member 3 are disposed between the two supporting parts 61 of the linking member 6, there is an advantage that it is possible to more reliably prevent the shafts 51 and 52 from falling with the high rigidity of the linking member 6 even in a case in which external forces in various directions act on the gripping part 120 provided at the first member 2.

Figure 7:
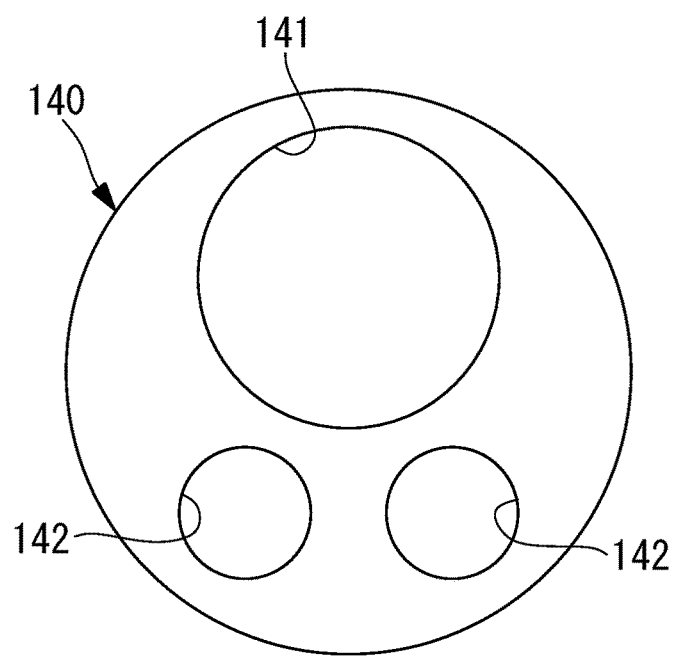
FIG. 7 is a horizontal sectional view illustrating an example of an overtube to which the manipulator in FIG. 1 is applied.

Also, according to the manipulator 100 in the present embodiment, the following advantages are achieved since the first joint 131 and the second joint 132 are bent in mutually opposite directions. That is, the manipulator 100 according to the present embodiment is inserted into each of two lumens 142 among three lumens 141 and 142 provided in an overtube 140 as illustrated in FIG. 7 and is used together with an endoscope 150 inserted into the other lumen 141.

Figure 8:
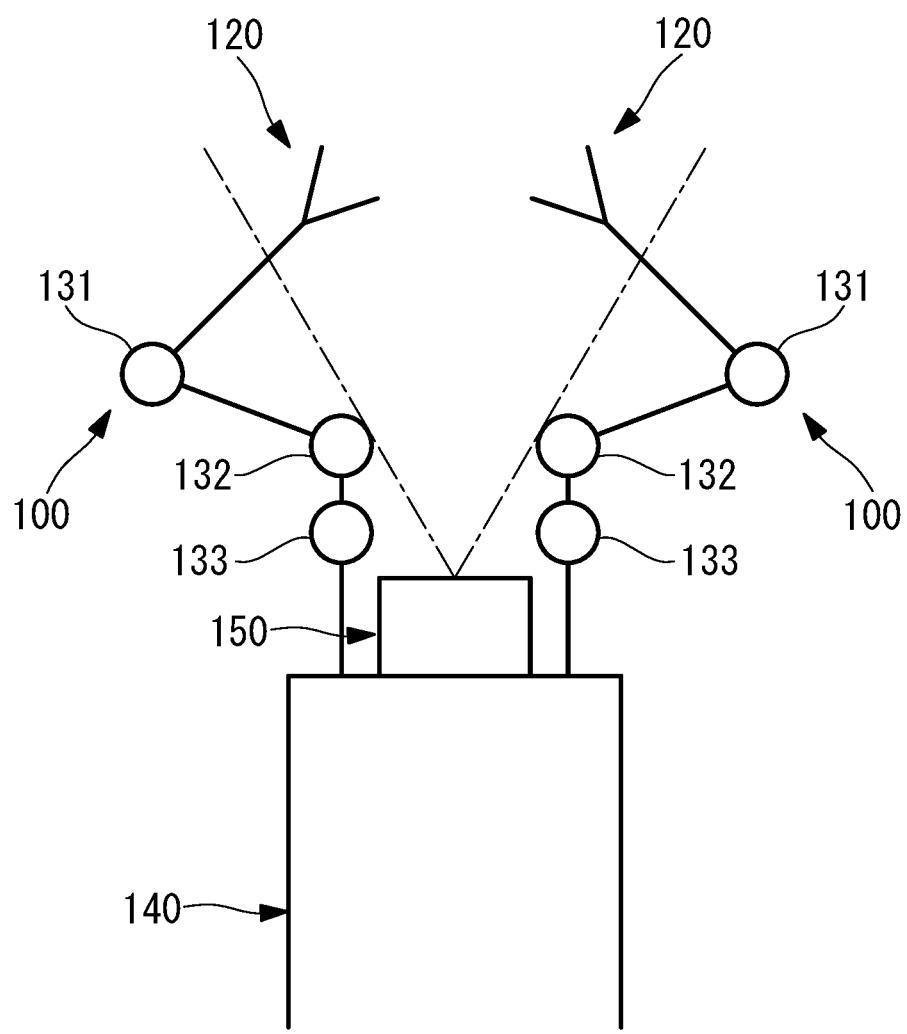
FIG. 8 is a schematic view illustrating a utilization state of the manipulator in FIG. 1 that is inserted into the overtube in FIG. 7 along with an endoscope.

In this case, by curving the second joint 132 in a direction deviating from the inside of a field of view of the endoscope 150, which is caused to project from a tip end of the overtube 140, and curving the first joint 131 in a direction in which the gripping part 120 is returned to the inside of the field of view as illustrated in FIG. 8, it is possible to prevent the manipulator 100 from interrupting the field of view of the endoscope 150 and to allow for a treatment on a target site with the gripping part 120 and the target site observed using the endoscope 150.

Also, since the manipulator 100 according to the present embodiment satisfies Conditional Expression (1), it is possible to constantly capture the gripping part 120 inside the field of view of the endoscope 150, to minimize the length of a hard part, to allow for operations in a narrow body cavity, and to cause the gripping part 120 to move to a desired position using the first joint 131 and the second joint 132.

In a case in which the manipulator 100 according to the present embodiment is applied to a needle holder for operating a curved needle, it is possible to suture a target tissue by changing the posture of the curved needle using the first joint 131, the second joint 132, and the third joint 133, adjusting the posture of the curved needle such that 80° to 90° is achieved with respect to the target site, and causing the needle to rotate in accordance with the curvature of the needle.

Figure 9:
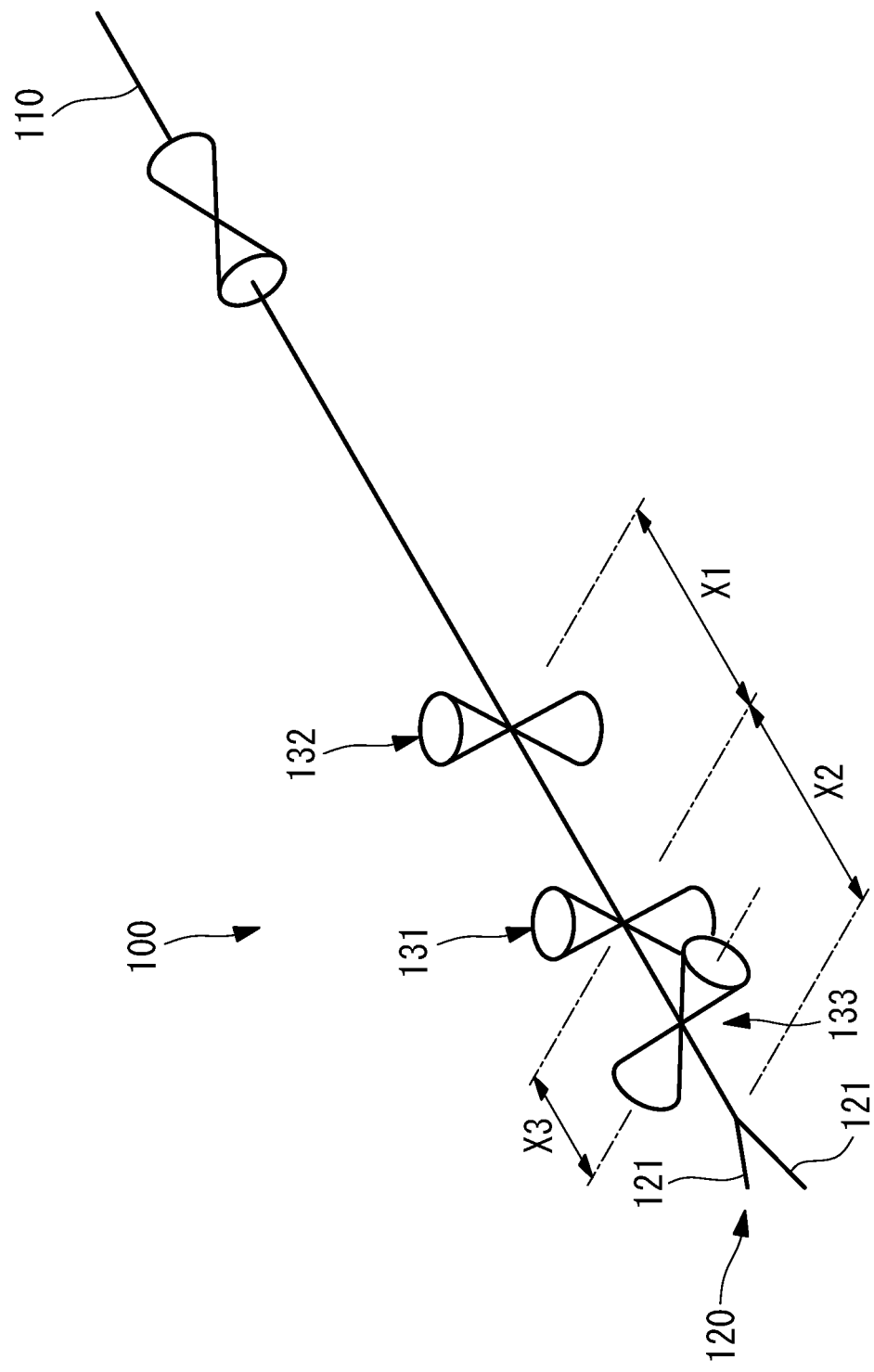
FIG. 9 is a schematic perspective view illustrating a shaft configuration of a manipulator according to an exemplary embodiment.
Figure 10:
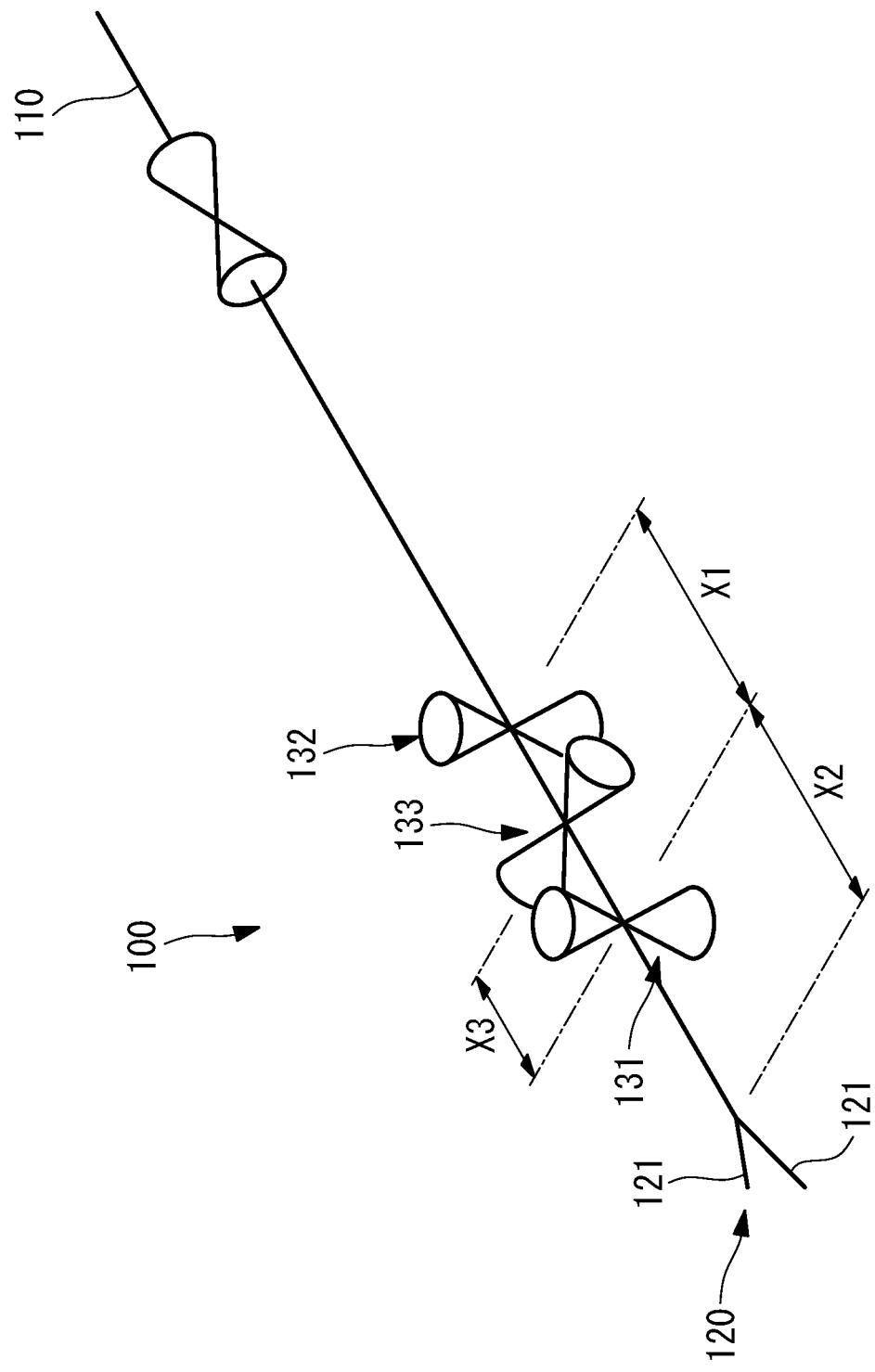
FIG. 10 is a schematic perspective view illustrating a shaft configuration of a manipulator according to an exemplary embodiment.

Also, although the first joint 131 and the second joint 132 are bending joints that bend in opposite directions along the same plane in the present embodiment, disposition of the first joint 131 to the third joint 133 may be replaced as illustrated in FIGS. 9 and 10 instead.

Next, a manipulator and a joint structure 101 thereof according to another exemplary embodiment will be described below with reference to drawings.

In description of the present embodiment, the same reference numerals will be given to parts with the same configurations as those of the manipulator 100 and the joint structure 1 thereof according to the aforementioned embodiment, and description thereof will be omitted.

Figure 11:
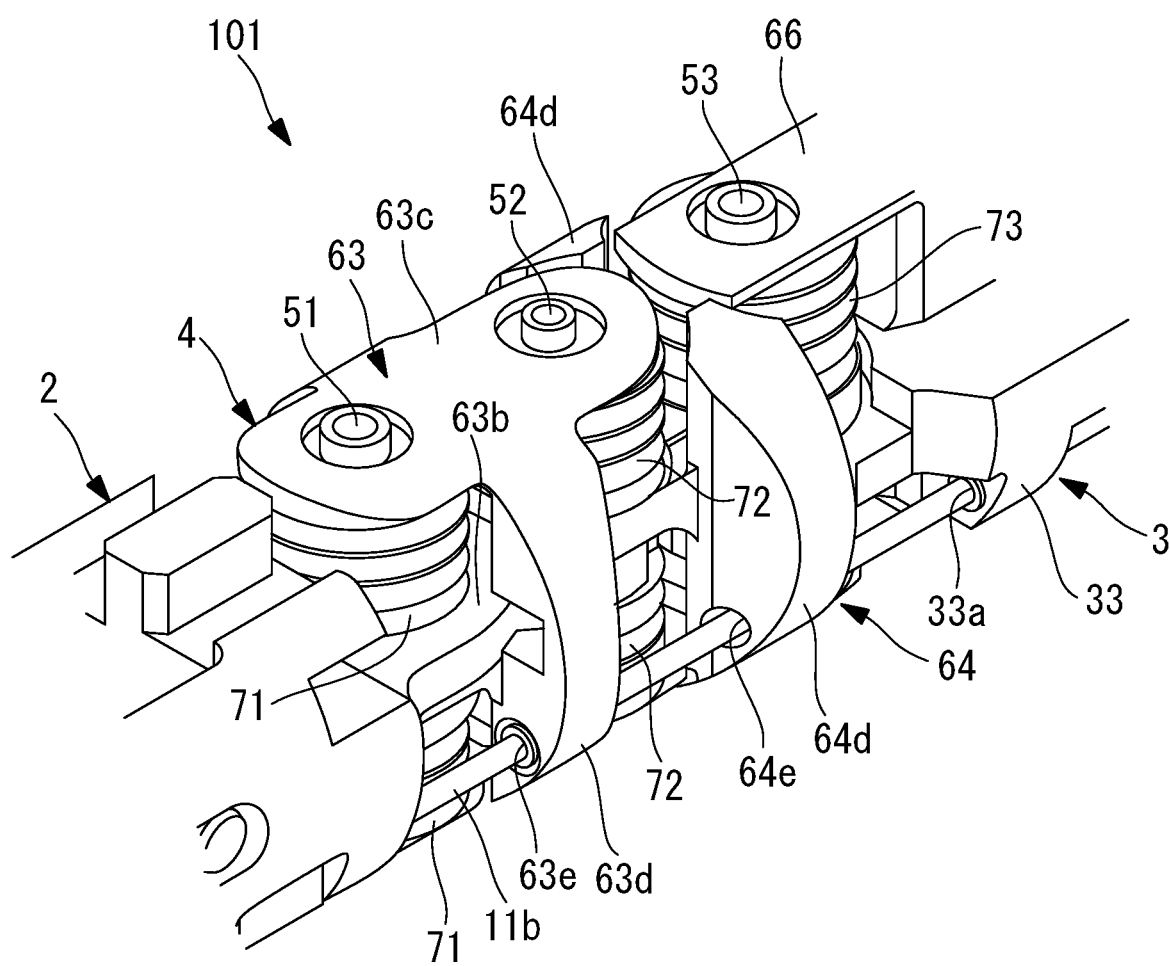
FIG. 11 is a partial perspective view illustrating a joint structure of a manipulator according to an exemplary embodiment.
Figure 12:
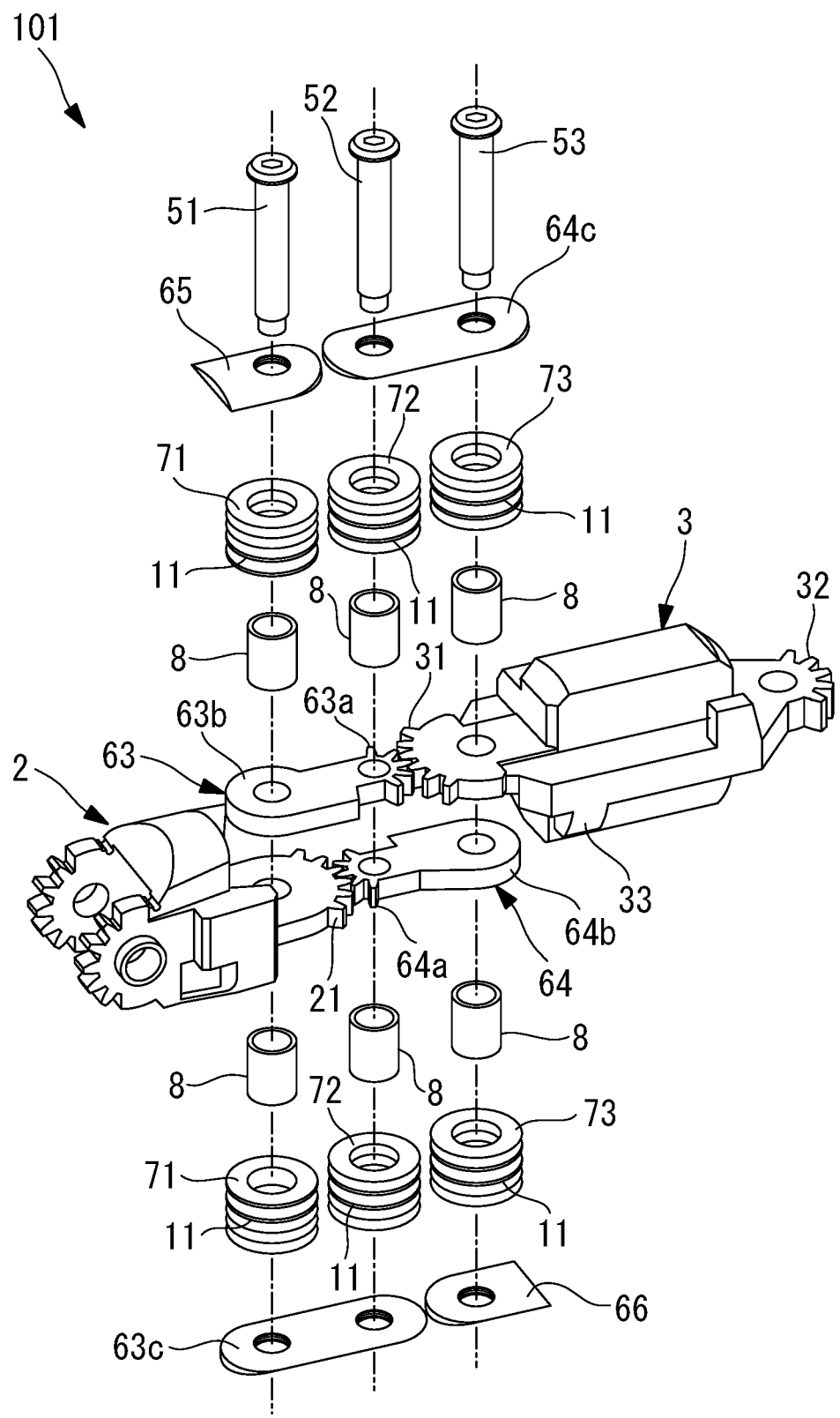
FIG. 12 is an exploded perspective view illustrating the joint structure in FIG. 11.

The joint structure 101 according to the present embodiment includes three shafts 51, 52, and 53 that are parallel to each other and two linking members 63 and 64 as illustrated in FIGS. 11 and 12.

Here, the shafts 51, 52, and 53 will be referred to as a first shaft 51, a second shaft 52, and a third shaft 53 from the tip end side for clear explanation. Also, the linking members 63 and 64 will be referred to as a first linking member 63 and a second linking member 64 from the tip end side.

The first linking member 63 and the second linking member 64 are coupled to each other so as to be able to swivel with the second shaft 52.

Also, the first linking member 63 includes, at an end thereof, a gear part (rolling part) 63a that is rotatably attached to the first shaft 51 and the second shaft 52 and that meshes with the second gear part 31 of the second member 3.

Figure 15:
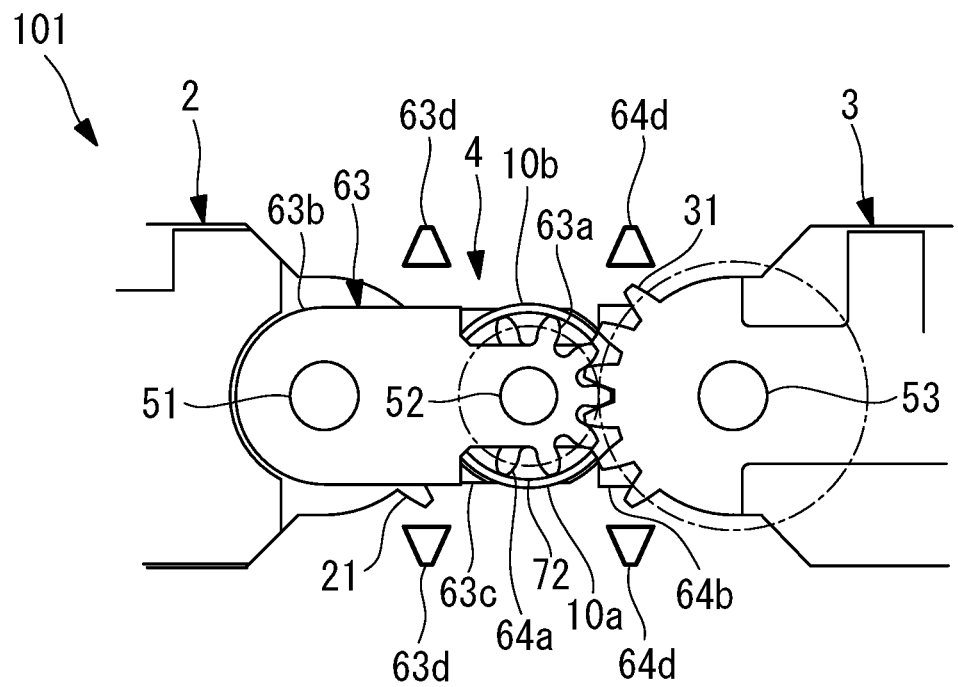
FIG. 15 is a partial side view for explaining meshing between a gear part of a first linking member and a second gear part of a second member in the joint structure in FIG. 11.
Figure 16:
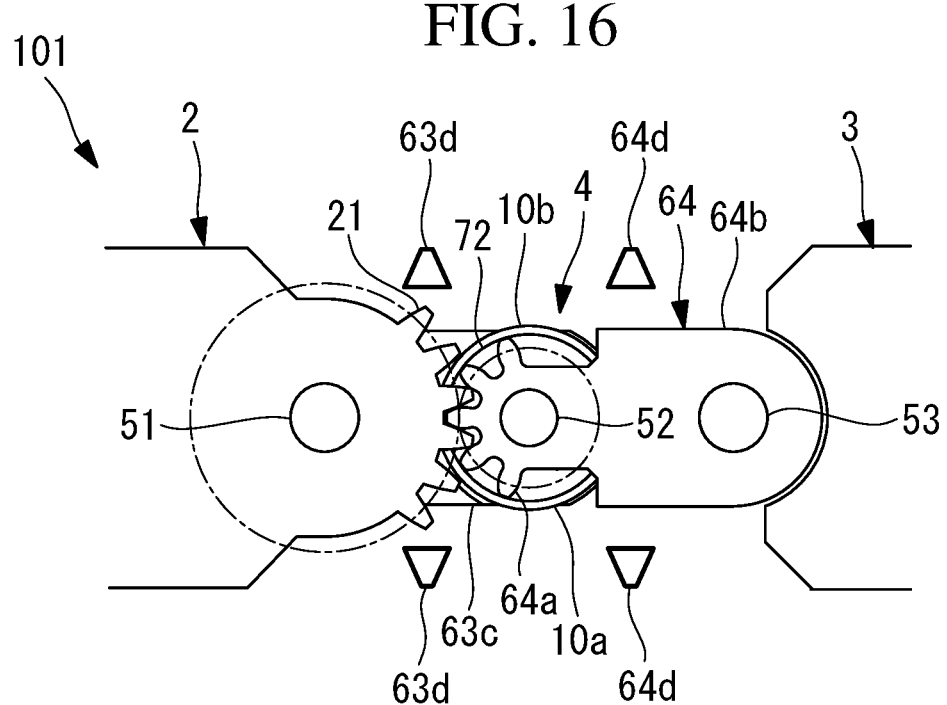
FIG. 16 is a partial side view for explaining meshing between a gear part of a second linking member and a first gear part of a first member in the joint structure in FIG. 11.
Figure 17:
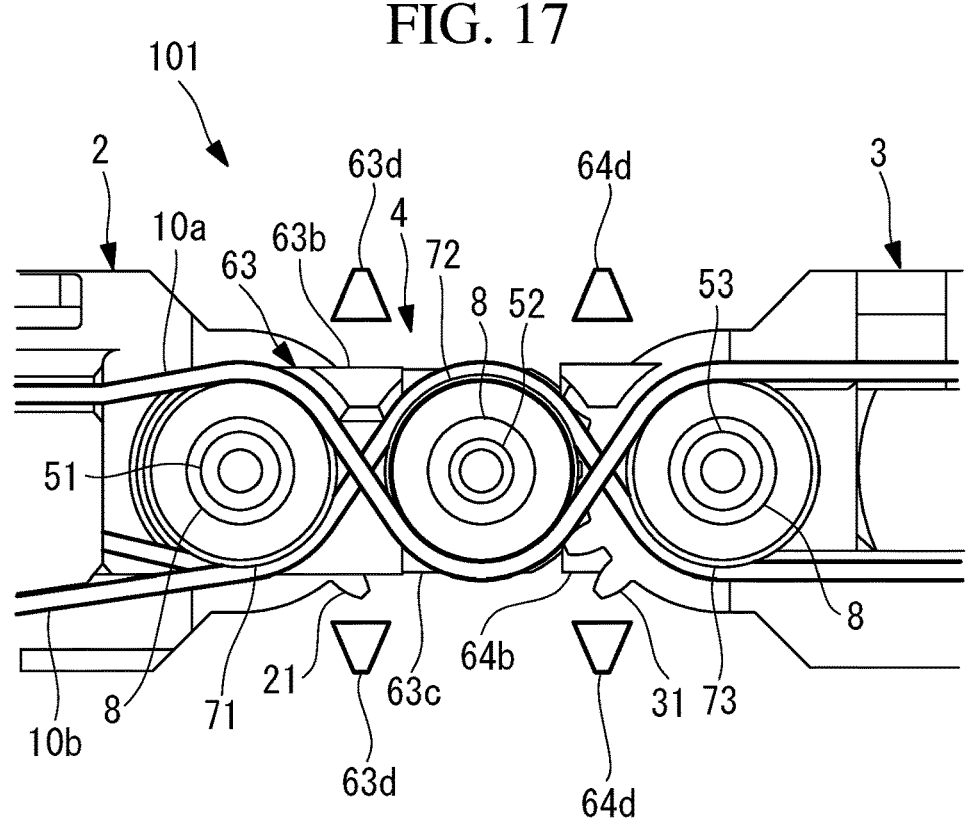
FIG. 17 is a partial side view illustrating a positional relationship of pulleys and a wire in the joint structure in FIG. 11.

In addition, the second linking member 64 includes, at an end thereof, a gear part (rolling part) 64a that is attached so as to be able to rotate about the second shaft 52 and the third shaft 53 and that meshes with the first gear part 21 of the first member 2, as illustrated in FIG. 15.

In the joint structure 101 according to the present embodiment, the first linking member 63 includes a first supporting part (supporting part) 63b that allows the first shaft 51 and the second shaft 52 to penetrate therethrough in a plate thickness direction and has a gear part 63a at one end, a second supporting part (supporting part) 63c that is disposed with the first gear part 21 of the first member 2 and the plurality of pulleys 71 and 72 sandwiched with the first supporting part 63b in the axial direction and that is attached to ends of the first shaft 51 and the second shaft 52, and a coupling part 63d that couples the first supporting part 63b to the second supporting part 63c, as illustrated in FIGS. 11 to 16. In FIG. 12, the reference numeral 65 represents a supporting member with a flat plate shape that allows the first shaft 51 to penetrate therethrough in a plate thickness direction, that is disposed with the single pulley 71 sandwiched with the first supporting part 63b in the axial direction, and that is attached to an end of the first shaft 51.

In FIG. 12, the first supporting part 63b and the second supporting part 63c are separately illustrated, and illustration of the coupling part 63d is omitted.

Also, the second linking member 64 has a structure that is similar to that of the first linking member 63 and includes a first supporting part 64b with a flat plate shape that allows the second shaft 52 and the third shaft 53 to penetrate therethrough in a plate thickness direction and that has a gear part 64a at an end, a second supporting part 64c that is disposed with the second gear part 31 of the second member 3 and a plurality of pulleys 72 and 73 with the first supporting part 64b in the axial direction and that is attached to ends of the second shaft 52 and the third shaft 53, and a coupling part 64d that couples the first supporting part 64b to the second supporting part 64c. In FIG. 12, the reference numeral 66 represents a supporting member with a flat plate shape that allows the third shaft 53 to penetrate therethrough in a plate thickness direction, that is disposed with a single pulley 73 sandwiched with the second supporting part 64c in the axial direction, and that is attached to an end of the third shaft 53.

Figure 13:
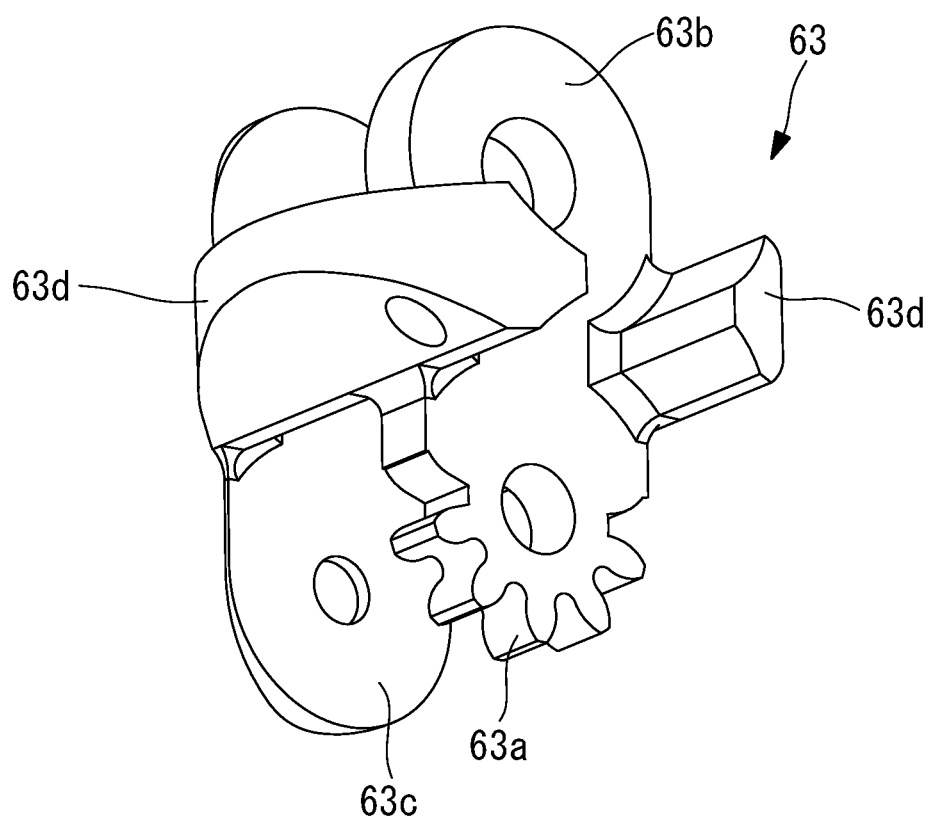
FIG. 13 is a perspective view illustrating an example of a linking member provided in the joint structure in FIG. 11.

Also, the coupling parts 63d and 64d of the first linking member 63 and the second linking member 64 are provided with through-holes 63e and 64e through which the two manipulation wires 11a and 11b are caused to penetrate, as illustrated in FIGS. 11 and 13.

In addition, one wire 10a is wound around the circumferential groove 11 of any of the three pulleys 71, 72, and 73 so as to alternately meander, and the other wire 10b is wound around the circumferential groove 11 of another one of the three pulleys 71, 72, and 73 so as to alternately meander in a direction opposite to that of the one wire 10a.

According to the joint structure 101 of the manipulator according to the present embodiment configured as described above, if the first member 2 is caused to swivel with respect to the second member 3 by pulling any one of the two manipulation wires 11a and 11b, the gear part 64a of the second linking member 64 that meshes with the first gear part 21 provided at the first member 2 rolls about the longitudinal axis of the first shaft 51, and the gear part 63a of the first linking member 63 that meshes with the second gear part 31 provided at the second member 3 rolls about the longitudinal axis of the third shaft 53.

Figure 18:
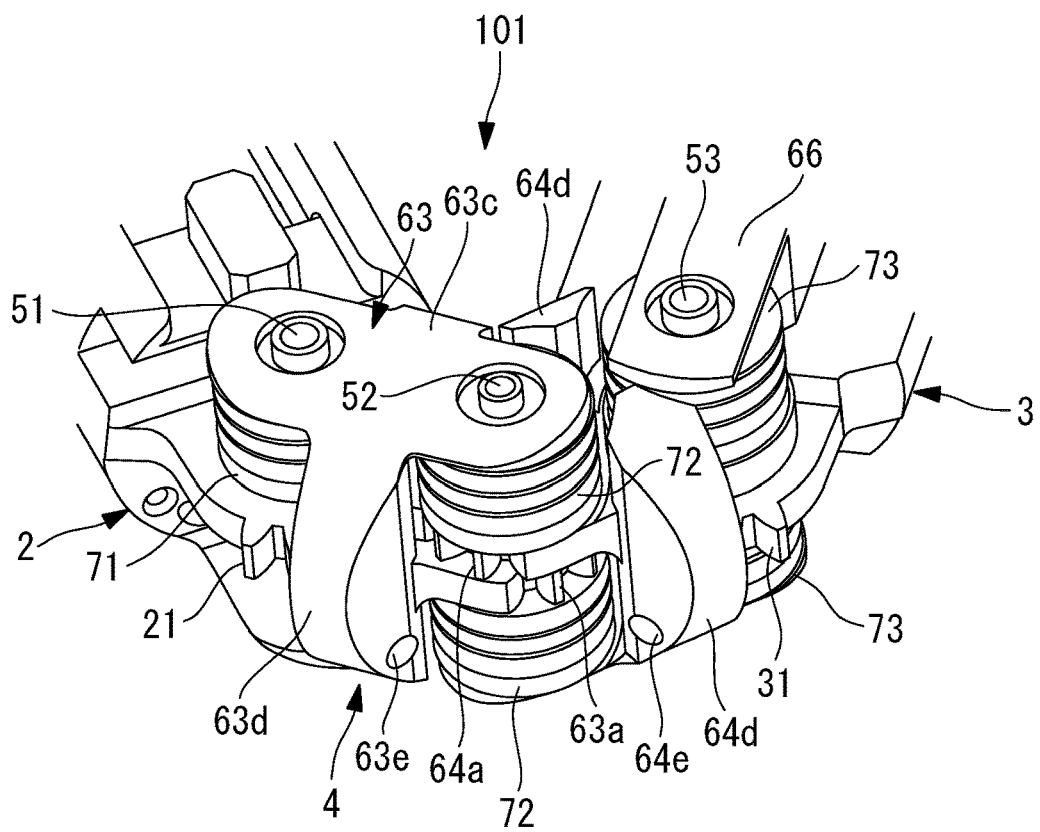
FIG. 18 is a perspective view illustrating a state in which the first member is caused to swivel with respect to the second member in the joint structure in FIG. 11.
Figure 19:
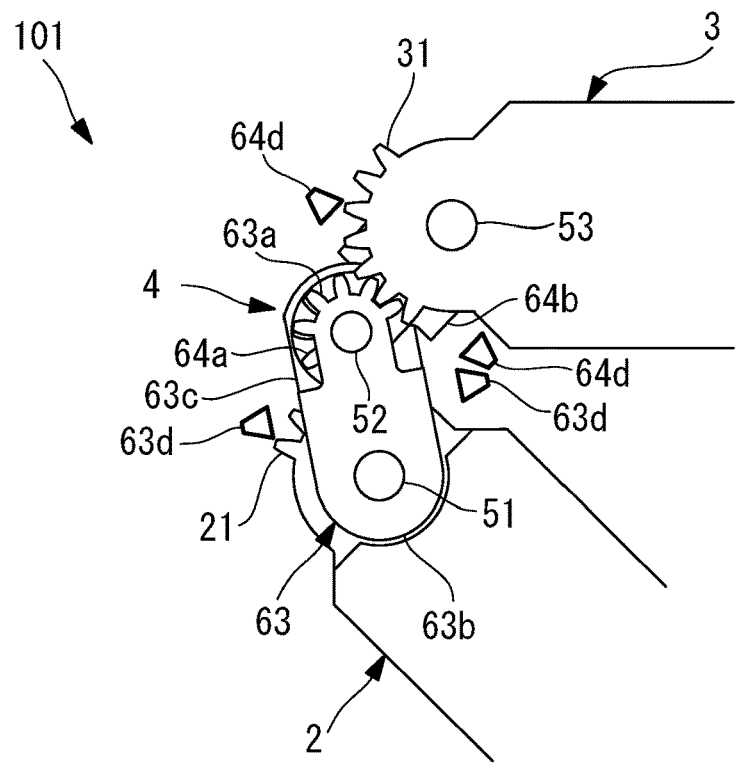
FIG. 19 is a side view illustrating a state in which the first member is caused to swivel with respect to the second member in the joint structure in FIG. 11.
Figure 20:
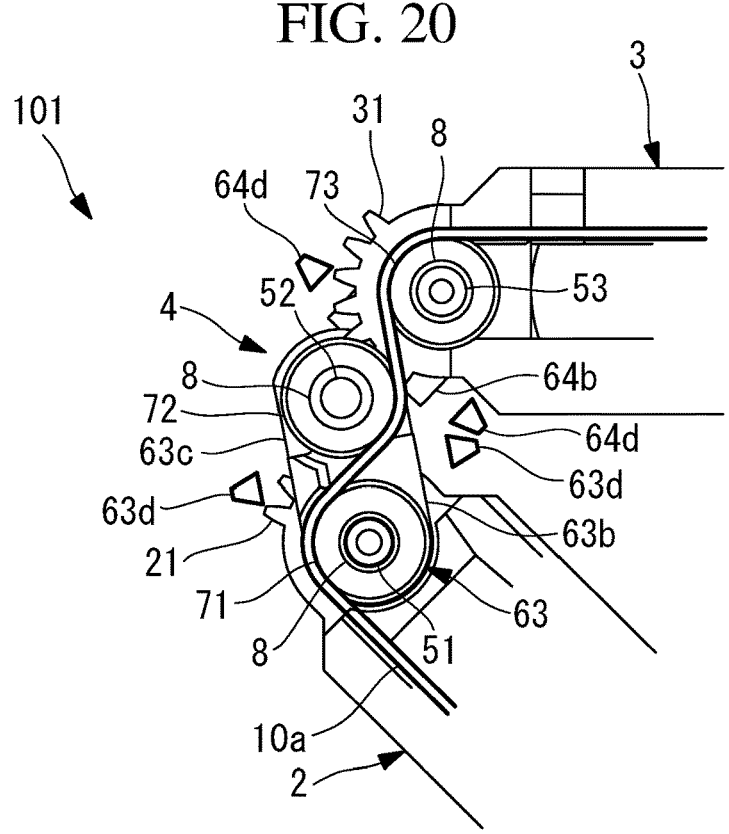
FIG. 20 is a side view illustrating a state of a wire when the first member is caused to swivel with respect to the second member in the joint structure in FIG. 11.

Consequently, the second linking member 64 attached to the second shaft 52 and the third shaft 53 so as to be able to swivel swivels about the longitudinal axis of the third shaft 53, and the first linking member 63 that is attached to the first shaft 51 and the second shaft 52 so as to be able to swivel swivels about the longitudinal axis of the second shaft 52, as illustrated in FIGS. 18 to 20.

The second shaft 52 is translated around the longitudinal axis of the third shaft 53 by the second linking member 64 swiveling, and the first shaft 51 is further translated around the longitudinal axis of the translated second shaft 52 by the first linking member 63 swiveling. Consequently, the second linking member 64 swivels with respect to the second member 3, the first linking member 63 swivels with respect to the second linking member 64, and the first member 2 swivels with respect to the first linking member 63, in the same direction.

That is, the first member 2 is caused to swivel with respect to the second member 3 at an angle obtained by summing up a swiveling angle of the second linking member 64 with respect to the second member 3, a swiveling member of the first linking member 63 with respect to the second linking member 64, and a swiveling member of the first member 2 with respect to the first linking member 63.

As a result, it is possible to cause the second member 3 to swivel with respect to the first member 2 at a large swiveling angle even if the swiveling angles of the respective linking members 63 and 64 are small. That is, there is an advantage that it is possible to reduce the swiveling angle among the first member 2, the linking members 63 and 64, and the second member 3, which are adjacent to each other, to avoid an interference, and to cause the second member 3 to largely swivel with respect to the first member 2.

In addition, since the respective linking members 63 and 64 dispose the supporting parts 63b, 63c, 64b, and 64c with flat plate shapes at positions at which the first gear part 21 or the second gear part 31 and the plurality of pulleys 71, 72, and 73 are sandwiched in the axial direction and couple all the supporting parts 63b, 63c, 64b, and 64c with the coupling parts 63d, and 64d in the joint structure 101 according to the present embodiment, there is an advantage that it is possible to form the linking members 63 and 64 with high rigidity and to prevent the shafts 51, 52, and 53 from falling with the wires 10a and 10b.

Figure 21:
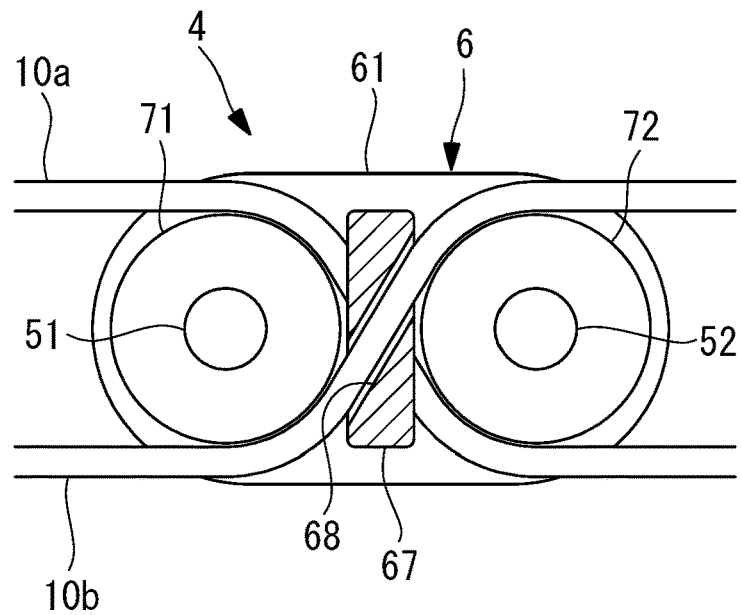
FIG. 21 is a side view in which a part illustrating a linking member provided with a coupling part according to an exemplary embodiment in which the joint structure in FIGS. 2 and 11 is cut away.
Figure 22:
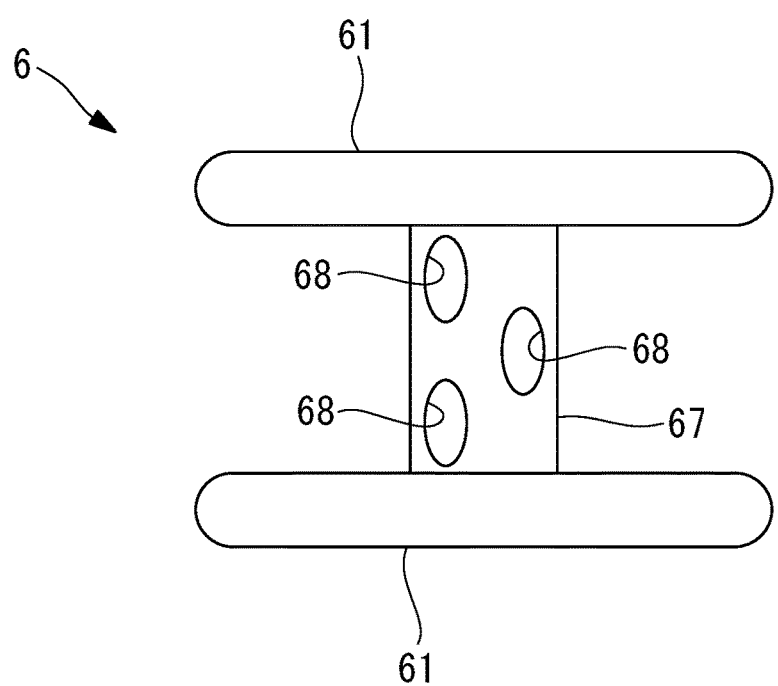
FIG. 22 is a front view of the linking member in FIG. 21.

Also, although the rigidity is enhanced with the ring-shaped transverse section configured by coupling the two supporting parts 61, 63b, 63c, 64b, 64c with flat plate shapes disposed at intervals with the coupling parts 62, 63d, and 64d at both ends in the width direction in the aforementioned embodiments, a coupling part 67 with a flat shape that couples the two supporting parts 61 between the two shafts 51 and 52 as illustrated in FIGS. 21 and 22 may be employed instead. In this case, the coupling part 67 may be provided with a plurality of guide holes 68 through which the plurality of wires 10a and 10b are caused to penetrate.

Figure 23:
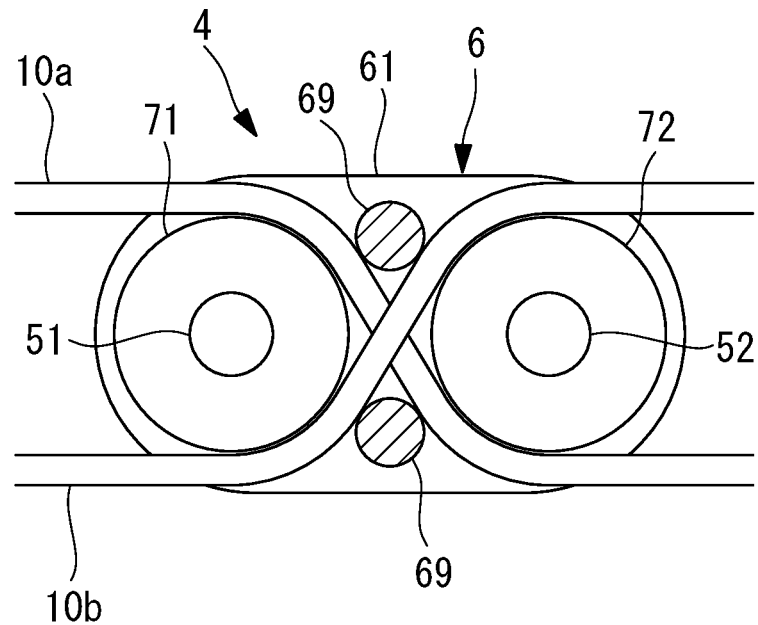
FIG. 23 is a side view in which a part illustrating a linking member provided with a coupling part according to an exemplary embodiment in which in the joint structure in FIGS. 2 and 11 is cut away.

Also, the two supporting parts 61 may be coupled with a pin (coupling part) 69 as illustrated in FIG. 23.

In addition, since the number of the wires 10a and 10b that pass through the respective joints 131, 132, and 133 and the number of the pulleys 71, 72, and 73 around which the wires 10a and 10b are wound are determined depending on the number of movable parts disposed on the tip end side beyond the joints, the numbers of the wires 10a and 10b and the pulleys 71, 72, and 73 decrease toward the joints disposed so as to be closer to the tip end side.

Figure 14:
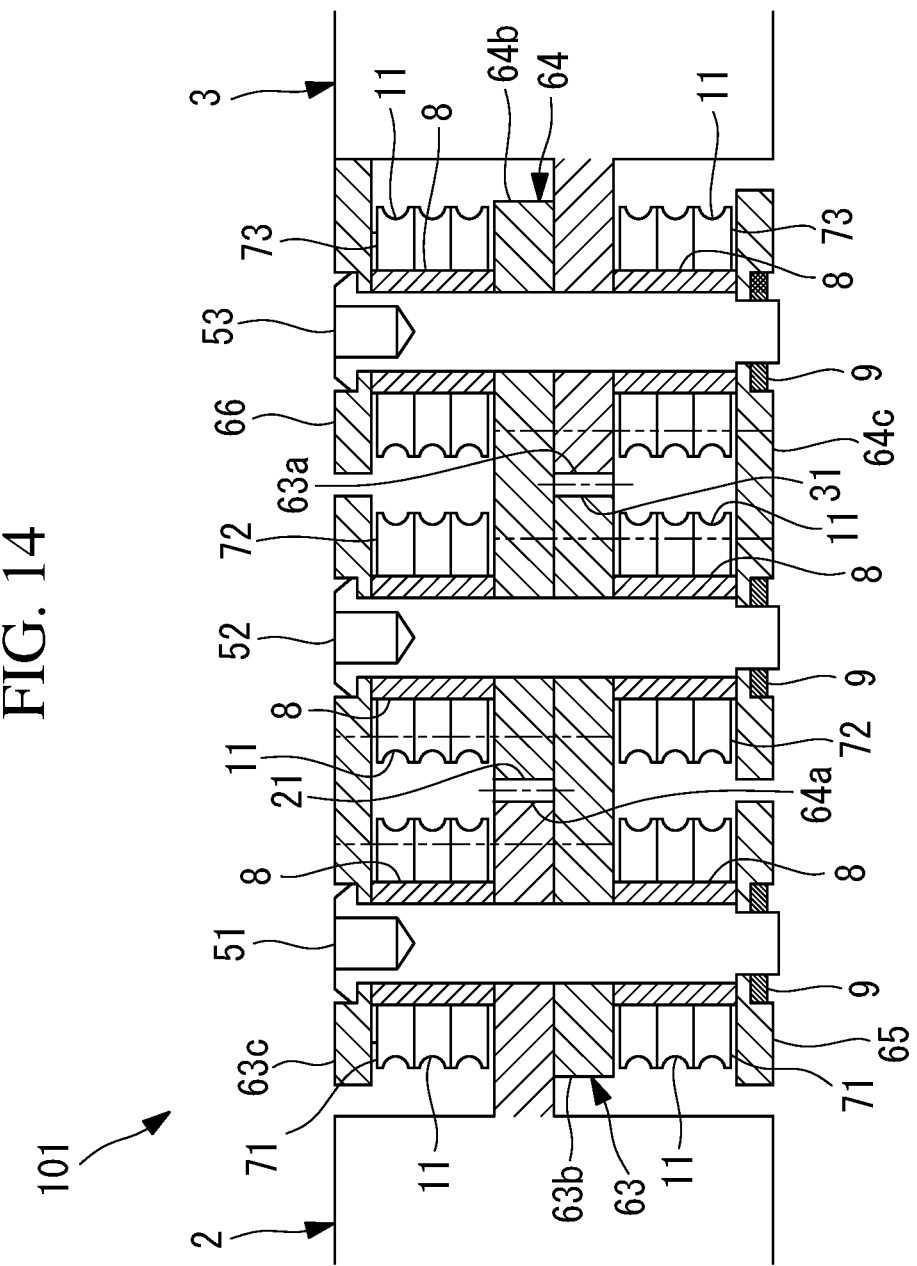
FIG. 14 is a partial vertical sectional view illustrating the joint structure in FIG. 11.
Figure 24:
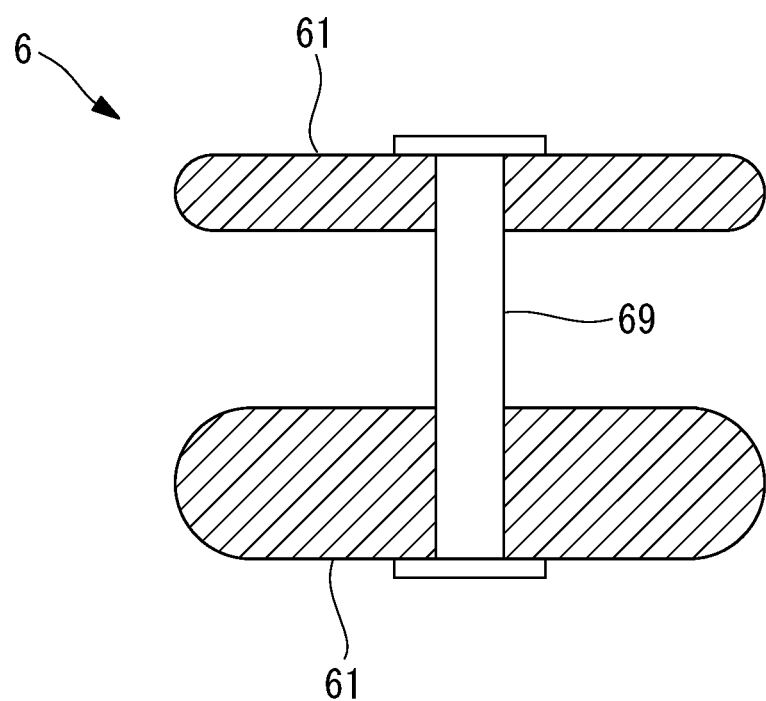
FIG. 24 is a vertical sectional view illustrating a linking member provided with a coupling part according to a joint structure according to an exemplary embodiment.

In the example illustrated in FIG. 1, for example, two wires 10a and 10b are sufficient to open and close the gripping part 120, and the number of the pulleys 71 and 72 may also be two, for the first joint 131 with only the gripping part 120 disposed at the tip end. Therefore, it is not necessary to provide four or six pulleys 71, 72, and 72 as illustrated in FIGS. 4 and 14, and the thicknesses of the supporting parts 61, 63b, 63c, 64b, and 64c may be configured to be thicker as illustrated in FIG. 24 instead of the pulleys 71, 72, and 72. Consequently, it is possible to further enhance rigidity of the linking members 6, 63, and 64 and thereby to further reliably prevent the shafts 51, 52, and 53 from falling.

Also, although the example in which an integral configuration of two of the supporting parts 61, 63b, 63c, 64b, and 64c and the coupling parts 62, 63d, 64d, and 67 has been described as the linking members 6, 63, and 64 in the aforementioned embodiment, integral linking members 6, 63, and 64 may be configured instead by coupling and attaching members divided into two parts in the direction of the longitudinal axes of the shafts 51, 52, and 53 in assembly. Arbitrary structures may be employed for the coupling parts 62, 63d, 64d, and 67. Coupling may be achieved by a snap-fit method that allows for one-touch coupling.

Although the manipulator 100 that has the gripping part 120 as an end effector at the tip end has been described as an example, another arbitrary end effector may be employed instead.

As a result, the above-described embodiment leads to the following aspects.

An aspect of the present disclosure is directed to a joint structure of a manipulator, including: two swiveling members that are coupled to each other so as to be able to swivel via a rolling contact; two or more shafts that constitute two or more bending joint parts between the swiveling members and that are parallel to each other; pulleys, which are supported so as to be able to rotate about longitudinal axes of the respective shafts, on which a wire is wound; and one or more linking members that are stretched between adjacent two of the shafts and that are attached so as to be able to swivel about the longitudinal axes of the respective shafts, in which the linking members include two supporting parts that are disposed at positions at which the pulleys are sandwiched therebetween in a direction of the longitudinal axes and a coupling part that couples the supporting parts to each other.

According to the present aspect, the one or more linking members are caused to swivel with respect to one of the swiveling members by one bending joint part formed of the shaft of one swiveling member, and the other swiveling member is caused to swivel with respect to the linking members by the other bending joint part formed of the shaft of the other swiveling member in a case in which the two swiveling members are caused to relatively swivel. Consequently, swiveling angles of the two or more bending joint parts are reduced by distributing a swiveling angle of the entire joint, and it is thus possible to cause the swiveling members to swivel at relatively large angles while curbing an interference between the swiveling members. Also, it is possible to secure the large swiveling angles while curbing a change in path length of the wire by stretching the wire over the pulleys provided at the respective shafts in a meandering manner.

If a traction force is applied to a base end of the wire in this state, the pulleys with the wire wound thereon are pressed by the traction force in a radial direction, and a bending force acts on shafts that support the pulleys.

According to the present aspect, since the linking members that are stretched over the two shafts and that are attached so as to be able to swivel about the longitudinal axes of the respective shafts include the supporting parts that are disposed on both sides of the pulleys in the direction of the longitudinal axes and the coupling part that couples the supporting parts, the bending force acts between support points of the two supporting parts of the linking member that are integrated by the coupling part. That is, since the shafts are supported in a double-supported beam form, and the bending force is received between the two support points, it is possible to improve rigidity with respect to the bending force and to apply an adequate traction force to the wire.

In the aforementioned aspect, the joint structure of a manipulator may further include: rolling parts at which the respective swiveling members are brought into a rolling contact with each other, the shafts may be disposed at two locations at rolling centers of the respective rolling parts, and the number of the linking members provided may be one.

In this manner, when the two swiveling members are caused to swivel with respect to each other with the rolling parts thereof brought into a rolling contact, the swiveling members are caused to swivel with the rolling contact maintained by the length of the single linking member stretched over the two shafts. The swiveling angle of the entire joint is distributed to the swiveling angles of the two bending joint parts formed of the two shafts, the respective swiveling angles are reduced, and it is thus possible to cause the swiveling members to swivel at a relatively large members while curbing an interference between the swiveling members.

Also, in the aforementioned aspect, the joint structure of a manipulator may further include: rolling parts at which the respective swiveling members are brought into a rolling contact with each other, the shafts may be disposed at three locations of rolling centers and a middle therebetween of the respective rolling parts, the number of the linking members provided may be two, the linking members being coupled to each other so as to be able to swivel with the shaft at the middle, and each of the linking members may be attached to the shaft disposed at the rolling center of any one of the swiveling members and may be brought into a rolling contact with the rolling part of the other swiveling member.

In this manner, if the linking member on the base end side is caused to swivel about the longitudinal axis of the shaft disposed at the rolling center of the swiveling member disposed on the base end side, the shaft at the middle that is supported by the linking member on the base end side is translated about the longitudinal axis of the shaft on the base end side while maintaining a distance between the shafts with the linking member on the base end side. Since the linking member on the tip end side supported by the shaft at the middle is in a rolling contact with the rolling part of the swiveling member on the base end side, swiveling with respect to the swiveling member on the base end side is caused by the rolling contact if the shaft at the middle is translated.

Consequently, the shaft on the tip end side that is supported by the linking member on the tip end side is translated about the longitudinal axis of the shaft at the middle while the distance between the shafts is maintained by the linking member on the tip end side. Since the linking member on the base end side is in a rolling contact with the rolling part of the swiveling member on the tip end side, swiveling with respect to the swiveling member on the tip end side is caused by the rolling contact if the shaft on the tip end side is translated.

In this manner, the swiveling angle of the entire joint is distributed to the swiveling angles of the three bending joint parts formed of the three shafts, the respective swiveling angles are reduced, and it is thus possible to cause the swiveling members to swivel at a relatively large angle while curbing an interference between the swiveling members.

Also, in the aforementioned aspect, the respective supporting parts may be disposed at positions at which any of the swiveling members is sandwiched therebetween in the direction of the longitudinal axes.

In this manner, it is possible to dispose the swiveling members between the supporting parts of the linking members with rigidity enhanced by the two supporting parts being coupled by the coupling part and to receive a bending force imparted on the swiveling members at positions with enhanced rigidity.

Another aspect of the present disclosure is directed to a manipulator, including: a gripping part that is provided at a tip end of an elongate inserting part; and a first joint and a second joint that are aligned in series between the inserting part and the gripping part and that have the aforementioned joint structure, in which the first joint that is disposed on a furthest side at the tip end is able to swivel at an angle that is greater than an angle at which the second joint on a base end side swivels, in a direction opposite to a direction in which the second joint swivels.

According to the present aspect, it is possible to bend the second joint on the base end side in a direction away from a field of view of an endoscope that has a field of view in which the gripping part of the manipulator can be observed, to bend the first joint on the tip end side in a direction returning to the inside of the field of view, to avoid the manipulator from occupying the field of view, and to facilitate observation of the gripping part at the tip end of the manipulator, a target site gripped with the gripping part, and the like, by using the gripping part of the manipulator along with the endoscope.

In the aforementioned aspect, the manipulator may further include: a third joint that is adjacent to the first joint or the second joint and that is able to swivel in a direction perpendicular to a swiveling direction of the first joint and the second joint, and the following conditional expressions may be satisfied:

$$X2 \geq X1 > X3$$

where X1 is a distance between the first joint and the second joint, X2 is a distance between the first joint and a base end of the gripping part, and X3 is a distance between the third joint and the first joint or the second joint that is closer to the third joint.

In this manner, it is possible to change an angle at a tip end of a curved needle gripped with the gripping part using the first to third joints, to cause the needle to pierce a target site at an angle of 80° to 90°, and to cause the needle to move along a rotating trajectory in accordance with a curvature of the curbed needle.

In this case, since bending rigidity of the shafts is enhanced with the linking member with high rigidity, it is possible to apply a large traction force and to firmly grip the curved needle with the gripping part.

Also, in the aforementioned aspect, the second joint may be able to swivel at 45° or more.

According to the present disclosure, effects that rigidity with respect to a bending force imparted on pulley shafts can be improved and an adequate traction force can be applied to a wire are achieved.

REFERENCE SIGNS LIST 1, 101 Joint structure
2 First member (swiveling member)
3 Second member (swiveling member)
4 Bending joint part
6 Linking member
10a, 10b Wire
21 First gear part (rolling part)
31 Second gear part (rolling part)
51 First shaft (shaft)
52 Second shaft (shaft)
53 Third shaft (shaft)
61 Supporting part
62, 63d, 64d, 67 Coupling part
63 First linking member (linking member)
63a, 64a Gear part (rolling part)
63b, 64b First supporting part (supporting part)
63c, 64c Second supporting part (supporting part)
64 Second linking member (linking member)
69 Pin (coupling part)
71, 72, 73 Pulley
100 Manipulator
110 Inserting part
120 Gripping part
131 First joint
132 Second joint
133 Third joint

The invention claimed is:

1. A joint structure of a manipulator, comprising:
first and second swiveling members that are coupled to each other so as to be able to swivel with respect to one another via a rolling contact;
first and second shafts that are parallel to each other, and define bending joints such that the first swiveling member is configured to swivel around the first shaft so as to be disposed at an angle with respect to the second swiveling member, and the second swiveling member is configured to swivel around the second shaft so as to be disposed at an angle with respect to the first swiveling member;
pulleys that are rotatably supported around the first and second shafts, a wire being wound around each of the pulleys; and
a connector that is attached to the first and second shafts so as to be able to swivel about a respective longitudinal axis of the first and second shafts, the connector including:
supports that are disposed on axial ends of the first and second shafts, so as to sandwich the pulleys therebetween in a direction of the longitudinal axis, and
a beam that extends in between the supports to couple the supports to each other at a position between the first and second shafts,
wherein:
the first swiveling member includes a first rolling part,
the second swiveling member includes a second rolling part,
the first and second swiveling members are in rolling contact with each other at the first rolling part and the second rolling part, and
the beam is arranged to overlap a region at which the first rolling part and the second rolling part are in rolling contact with each other, in a direction orthogonal to the longitudinal axis of the first and second shafts.

2. The joint structure according to claim 1, wherein the connector comprises two beams that are coupled to opposite sides of the supports at a position between the first and second shafts in the direction orthogonal to the longitudinal axis of the first and second shafts.

3. The joint structure according to claim 1, wherein:
the first and second shafts are respectively disposed at first and second rolling centers of the first and second rolling parts of the first and second swiveling members, respectively.

4. The joint structure according to claim 1, further comprising:
a third shaft parallel to the first and second shafts, wherein:
the first, second, and third shafts are disposed at one of three locations:
a rolling center of the first rolling part of the first swiveling member,
a rolling center of the second rolling part of the second swiveling member, and
in between the rolling centers of the first and second rolling parts of the first and second swiveling members, and
the connector is configured so as to be able to swivel with a middle shaft of the first, second, and third shafts.

5. The joint structure according to claim 4, wherein the first and second shafts are disposed at a respective rolling center of the first and second rolling parts of the first and second swiveling members, and the third shaft is disposed in between the first and second shafts.

6. The joint structure according to claim 5, wherein:
the supports of the connector include:
a first support coupled to upper axial ends of the first and third shafts,
a second support coupled to an upper axial end of the second shaft,
a third support coupled to a lower axial end of the first shaft, and a fourth support coupled to a lower axial end of the third and second shafts, the first and third supports are coupled by a beam positioned between the first and third shafts, the second and fourth supports are coupled by a beam positioned between the third and second shafts.

7. The joint structure according to claim 1, wherein the first and second swiveling members are sandwiched between at least two of the supports of the connector in the direction of the longitudinal axis.

8. A manipulator comprising:

a grip that is provided at a tip end of an elongate insertion part; and a first joint and a second joint that are aligned in series between the insertion part and the grip and that have the joint structure according to claim 1, wherein:

the first joint is disposed adjacent to the tip end, and the second joint is disposed on a base end side of the first joint, and the first joint is configured to swivel at an angle that is greater than a swiveling angle of the second joint in a direction opposite to a direction in which the second joint swivels.

9. The manipulator according to claim 8, further comprising:

a third joint that is adjacent to the first joint or the second joint and that is configured to swivel in a direction perpendicular to a swiveling direction of the first joint and the second joint, wherein the following conditional expressions are satisfied:

$$X2 \geq X1 > X3$$

where:

X1 is a distance between the first joint and the second joint,

X2 is a distance between the first joint and a base end of the grip,

X3 is a distance between the third joint and the first joint or the second joint that is closer to the third joint.

10. The manipulator according to claim 8, wherein the second joint is able to swivel at an angle of 45° or more.

* * * * *